United States Patent [19]

Agostini et al.

[11] Patent Number: 5,440,064

[45] Date of Patent: Aug. 8, 1995

[54] PROCESS FOR THE PREPARATION OF ORGANOSILICON DISULFIDE COMPOUNDS

[75] Inventors: Giorgio Agostini, Cruchten, Luxembourg; Leon E. E. Christiaens, Nandrin, Belgium; Uwe E. Frank, Ettelbruck, Luxembourg; Thierry F. E. Materne, Attert; Vincent L. A. Tadino, Liege, both of Belgium; Friedrich Visel, Bofferdange; Rene J. Zimmer, Howald, both of Luxembourg

[73] Assignee: The Goodyear Tire & Rubber Company, Akron, Ohio

[21] Appl. No.: 363,110

[22] Filed: Dec. 23, 1994

[51] Int. Cl.⁶ .................................. C07F 7/08
[52] U.S. Cl. .................................. 556/427
[58] Field of Search ........................ 556/427

[56] References Cited

U.S. PATENT DOCUMENTS

| | | | |
|---|---|---|---|
| 4,383,132 | 5/1983 | Schwarz et al. | 556/427 |
| 4,408,464 | 10/1983 | Schwarz et al. | 556/427 |
| 4,507,490 | 3/1985 | Panster et al. | 556/427 |
| 4,595,740 | 6/1986 | Panster | 556/427 X |

*Primary Examiner*—Paul F. Shaver
*Attorney, Agent, or Firm*—Bruce J. Hendricks

[57] ABSTRACT

The present invention relates to a process for the preparation of organo silicon disulfide compounds. The process involves oxidizing a mercaptoalkoxysilane in the presence of manganese dioxide.

10 Claims, No Drawings

PROCESS FOR THE PREPARATION OF ORGANOSILICON DISULFIDE COMPOUNDS

BACKGROUND OF THE INVENTION

The present invention relates to a process for the preparation of organo silicon disulfide compounds. Organo silicon disulfides are known adhesion promoters in sulfur-vulcanizable rubber mixtures reinforced with inorganic materials such as glass $SiO_2$, aluminosilicates and carbon black. For example, in GB 1,484,909, there is disclosed a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

Generally speaking, organosilicon disulfide compounds are very expensive and, with the increasing interest in silica-reinforced vulcanizable rubber, more cost-efficient methods of preparing these compounds are needed.

SUMMARY OF THE INVENTION

The present invention relates to a process for the preparation of a organosilicon disulfide compounds of the formula $$Z-R^1-S_2-R^1-Z \qquad I$$

comprising oxidizing a compound of the formula $$Z-R^1-SH \qquad II$$

in the presence of manganese dioxide, wherein Z is selected from the group consisting of

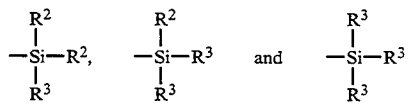

wherein $R^2$ may be the same or different and is independently selected from the group consisting of an alkyl group having 1 to 4 carbons and phenyl; $R^3$ may be the same or different and is independently selected from the group consisting of alkyl groups having 1 to 4 carbon atoms, phenyl, alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

DETAILED DESCRIPTION OF THE INVENTION

The present invention relates to a process for the preparation of organosilicon disulfide compounds. Representative organosilicon disulfide compounds of formula I which may be prepared in accordance with the present invention include 2,2'-bis(trimethoxysilylethyl) disulfide; 3,3'-bis(trimethoxysilylpropyl) disulfide; 3,3'-bis(triethoxysilylpropyl) disulfide; 2,2'-bis(triethoxysilylpropyl) disulfide; 3,3'-bis(triethoxysilylpropyl) disulfide; 2,2'-bis(tripropoxysilylethyl) disulfide; 2,2'-bis(trisec.butoxysilylethyl) disulfide; 3,3'-bis(tri-t-butoxyethyl) disulfide; 3,3'-bis(triisopropoxypropyl) disulfide; 3,3'-bis(trioctoxypropyl) disulfide; 2,2'-bis(2'-ethylhexoxysilylethyl) disulfide; 2,2'-bis(dimethoxy ethoxysilylethyl) disulfide; 3,3'-bis(methoxyethoxypropoxysilylpropyl) disulfide; 3,3'-bis(dimethoxymethylsilylpropyl) disulfide; 3,3'-bis(methoxy dimethylsilylpropyl) disulfide; 3,3'-bis(cyclohexoxy dimethylsilylpropyl) disulfide; 4,4'-bis(trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis(trimethoxysilylcyclohexyl) disulfide; 12,12'-bis(trimethoxysilyldodecyl) disulfide; 12,12'-bis(triethoxysilyldodecyl) disulfide; 18,18'-bis(trimethoxysilyloctadecyl) disulfide; 18,18'-bis(methoxydimethylsilyloctadecyl) disulfide; 2,2'-bis(trimethoxysilyl-2-methylethyl) disulfide; 2,2'-bis(triethoxysilyl-2-methylethyl) disulfide; 2,2'-bis(tripropoxysilyl-2-methylethyl) disulfide; 2,2'-bis(trioctoxysilyl-2-methylethyl) disulfide; 2,2'-bis(trimethoxysilyl-phenyl) disulfide; 2,2'-bis(triethoxysilyl-phenyl) disulfide; 1,1'-bis(trimethoxysilyl-tolyl)disulfide; 1,1'-bis(triethoxysilyl-tolyl)disulfide; 1,1'-bis(trimethoxysilyl-methyl tolyl) disulfide; 1,1'-bis(triethoxysilyl-methyl tolyl) disulfide; 2,2'-bis(trimethoxysilyl-ethyl phenyl) disulfide; 2,2'-bis(triethoxysilyl-ethyl phenyl) disulfide; 2,2'-bis(trimethoxysilyl-ethyl tolyl) disulfide; 2,2'-bis(triethoxysilyl-ethyl tolyl) disulfide; 3,3'-bis(trimethoxysilyl-propyl phenyl) disulfide; 3,3'-bis(triethoxysilyl-propyl phenyl) disulfide; 3,3'-bis(trimethoxysilyl-propyl tolyl) disulfide; and 3,3'-bis(triethoxysilyl-propyl tolyl) disulfide.

With reference to formula I, preferably $R^1$ is a alkylene group having 1 to 3 carbon atoms Z is

ps and $R^3$ is an alkoxy group having from 1 to 2 carbon atoms.

The desired products are prepared by oxidizing a compound of formula II. Representative examples of compounds of formula II include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec.butoxysilane, 3-mercaptopropyl tri-t-butoxysilane, 3-mercaptopropyl triisopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl cyclohexoxy dimethyl silane, 4-mercaptobutyl trimethoxysilane, 3-mercapto-3-methylpropyl-trimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyltriethoxysilane, 2-mercapto-2-methylethyltripropoxysilane, 2-mercapto-2-methylethyltrioctoxysilane, 2-mercaptophenyl trimethoxysilane, 2-mercaptophenyl triethoxysilane; 1-mercaptotolyl trimethoxysilane; 1-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

With reference to formula II, preferably Z is

$R^3$ is an alkoxy group having from 1 to 2 carbon atoms and $R^1$ is an alkylene group having 2 to 3 carbon atoms.

The mercapto compound of formula II is oxidized in the presence of manganese dioxide. Whereas commercially available manganese dioxide may be used, it is preferred to use freshly prepared manganese dioxide. Manganese dioxide may be prepared by adding an aqueous suspension of $MnSO_4 \cdot H_2O$ and sodium hydroxide to aqueous solution of $KMnO_4$. The mixture is allowed to react, the precipitate is isolated, washed and then dried. To increase the surface area of the manganese dioxide product, it is preferred to grind the manganese dioxide before use. Another way to significantly increase the active $MnO_2$ surface is to deposit the oxide onto an inert carrier like silica, alumosilicates, charcoal and the like. It has also been discovered that, after the manganese dioxide has been used in the process of the present invention, the isolated manganese dioxide is preferably regenerated. The manganese dioxide may be regenerated by drying the manganese dioxide at 120° C. The manganese dioxide may also be regenerated by adding the manganese dioxide to a boiling mixture of water and Norvanol ®. Norvanol ® is a commercially available mixture of 83 percent ethanol, 3 percent ether and 14 percent water. After a suitable time, such as 2 hours, the manganese dioxide is isolated, washed and dried at 120° C.

The process of the present invention involves oxidizing the compound of formula II in the presence of manganese dioxide. The molar ratio of the compound of formula II to manganese dioxide may range from 1:0.025 to 1:45. Preferably, the molar ratio ranges from 1:0.5 to 1:25 with a range of from 1:4 to 1:1.7 being particularly preferred.

The oxidation reaction should be conducted in the absence of water because the presence of a siloxane moiety may be hydrolysed by contact with water.

The oxidation reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichloroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, cyclohexane and toluene.

The oxidation reaction may be conducted over a variety of temperatures. Generally speaking, the oxidation reaction is conducted in a temperature ranging from 20° C. to 100° C. Preferably, the reaction is conducted at a temperature ranging from 50° C. to 90° C.

The process of the present invention may be conducted at a variety of pressures. Generally speaking, however, the oxidation reaction is conducted at a pressure ranging from 0.096 to 4.83 $kg/cm^2$.

EXAMPLE 1

Synthesis of Manganese Dioxide

Into the reaction vessel was added an aqueous solution of 31.6 grams (0.2 mole) of $KMnO_4$ (200 ml of water). The solution was vigorously stirred to which was added a suspension of 50.7 grams (0.3 mole) of $MnSO_4 \cdot H_2O$, 20 grams (0.2 mole) of NaOH and 200 ml of water. Stirring was continued for one hour. The precipitate was isolated, washed with water and dried at 120° C. The dried product was ground to a fine powder.

EXAMPLE 2

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic graphic analysis. The purity was determined to exceed 95 percent of desired product.

EXAMPLE 3

Preparation of bis(triethoxysilylpropyldisulfide)

In a 2-liter beaker, 4,567 grams (52.5 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 4

Preparation of bis(triethoxysilylpropyldisulfide)

In a 2-liter beaker, 3,654 grams (42 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 5

Preparation of bis(triethoxysilylpropyldisulfide)

In a 2-liter beaker, 2,740 grams (31.5 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 6

Preparation of bis(triethoxysilylpropyldisulfide)

In a 2-liter beaker, 1,827 grams (21 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 7

Preparation of bis(triethoxysilylpropyldisulfide)

In a 2-liter beaker, 913.5 grams (10.5 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 8

Preparation of bis(triethoxysilylpropyldisulfide)

In a 2-liter beaker, 365.4 grams (4.2 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 9

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of dichloromethane were added. Stirring continued for an additional one hour. The solid was filtered and washed with dichloromethane. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 10

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of carbon tetrachloride were added. Stirring continued for an additional one hour. The solid was filtered and washed with carbon tetrachloride. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 11

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of dichloroethylene were added. Stirring continued for an additional one hour. The solid was filtered and washed with dichloroethylene. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 12

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of trichloroethylene were added. Stirring continued for an-additional one hour. The solid was filtered and washed with trichloroethylene. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 13

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of toluene were added. Stirring continued for an additional one hour. The solid was filtered and washed with toluene. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 14

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of xylene were added. Stirring continued for an additional one hour. The solid was filtered and washed with xylene. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 15

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of benzene were added. Stirring continued for an additional one hour. The solid was filtered and washed with benzene. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 16

Preparation of bis(triethoxysilypropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of heptane were added. Stirring continued for an additional one hour. The solid was filtered and washed with heptane. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 17

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of cyclohexane were added. Stirring continued for an additional one hour. The solid was filtered and washed with cyclohexane. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 18

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of hexane were added. Stirring continued for an additional one hour. The solid was filtered and washed with hexane. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 19

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of tetrahydrofuran were added. Stirring continued for an additional one hour. The solid was filtered and washed with tetrahydrofuran. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 20

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of dioxane were added. Stirring continued for an additional one hour. The solid was filtered and washed with dioxane. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 21

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 500 ml of diisopropyl ether were added. Stirring continued for an additional one hour. The solid was filtered and washed with diisopropyl ether. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 22

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 70° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 23

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about 50° C., 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

EXAMPLE 24

Preparation of bis(triethoxysilylpropyldisulfide)

In a 2-liter beaker, 320 grams (3.68 mole) of $MnO_2$ were placed. Thereafter, 500 grams (2.1 mole) of 3-mercaptopropyl triethoxysilane were slowly added. During the period of addition, the reaction mixture was vigorously stirred. When the reaction reached about room temperature, 500 ml of chloroform were added. Stirring continued for an additional one hour. The solid was filtered and washed with chloroform. The organic phase was filtered on charcoal to eliminate all the $MnO_2$. The solvent was evaporated under reduced pressure to obtain 470 grams (0.99 mole) of product. The product was subjected to gas chromatographic analysis. The purity was determined to exceed 95 percent of desired product.

Control

EXAMPLE 1

Preparation of bis(triethoxysilylpropyldisulfide)

In a 4-liter beaker, 1,004 grams (4.2 mole) of $PbO_2$ were placed. Thereafter, 500 grams (2.1 mole) of 3-mercaptopropyl triethoxysilane were slowly added. During the period of addition, the reaction mixture was vigorously stirred. When the reaction reached about 90° C., 1,500 ml of toluene were added. Stirring continued for an additional one hour at 110° C. After the one hour, a gas chromatographic analysis was done and the conversion of mercaptan to disulfide did not exceed 30 percent. During the next 8 hours, the reaction continued without further conversion of the mercaptan to the disulfide.

Control

EXAMPLE 2

Preparation of bis(triethoxysilylpropyldisulfide)

In a 2-liter beaker, 420 grams (4.2 mole) of $CrO_3$ were placed. Thereafter, 500 grams (2.1 mole) of 3-mercaptopropyl triethoxysilane were slowly added. During the period of addition, the reaction mixture was vigorously stirred. When the reaction reached about 90° C., 1,500 ml of toluene were added. Stirring continued for an additional one hour at 110° C. After the one hour, a gas chromatographic analysis was done and the conversion of mercaptan to disulfide did not exceed 23 percent. During the next 8 hours, the reaction continued without further conversion of the mercaptan to the disulfide.

Control

EXAMPLE 3

Preparation of bis(triethoxysilylpropyldisulfide)

In a 3-liter beaker, 672 grams (4.2 mole) of $Fe_2O_3$ were placed. Thereafter, 500 grams (2.1 mole) of 3-mercaptopropyl triethoxysilane were slowly added. During the period of addition, the reaction mixture was vigorously stirred. When the reaction reached about 90° C., 1,000 ml of toluene were added. Stirring continued for an additional one hour at 110° C. After the one hour, a gas chromatographic analysis was done and the conversion of mercaptan to disulfide did not exceed 25 percent. During the next 8 hours, the reaction continued without further conversion of the mercaptan to the disulfide.

Control

EXAMPLE 4

Preparation of bis(triethoxysilylpropyldisulfide)

In a 3-liter beaker, 697 grams (4.2 mole) of $CrO_3$ were placed. Thereafter, 500 grams (2.1 mole) of 3-mercaptopropyl triethoxysilane were slowly added. During the period of addition, the reaction mixture was vigorously stirred. When the reaction reached about 90° C., 1,000 ml of toluene were added. Stirring continued for an additional one hour at 110° C. After the one hour, a gas chromatographic analysis was done and the conversion of mercaptan to disulfide did not exceed 19 percent. During the next 8 hours, the reaction continued without further conversion of the mercaptan to the disulfide.

Control

EXAMPLE 5

Preparation of bis(triethoxysilylpropyldisulfide)

In a 2-liter beaker, 334 grams (4.2 mole) of CuO were placed. Thereafter, 500 grams (2.1 mole) of 3-mercaptopropyl triethoxysilane were slowly added. During the period of addition, the reaction mixture was vigorously stirred. When the reaction reached about 90° C., 1,000 ml of toluene were added. Stirring continued for an additional one hour at 110° C. After the one hour, a gas chromatographic analysis was done and the conversion of mercaptan to disulfide did not exceed 26 percent. During the next 8 hours, the reaction continued without further conversion of the mercaptan to the disulfide.

Control

EXAMPLE 6

Preparation of bis(triethoxysilylpropyldisulfide)

In a 2-liter beaker, 428.4 grams (4.2 mole) of $Al_2O_3$ were placed. Thereafter, 500 grams (2.1 mole) of 3-mercaptopropyl triethoxysilane were slowly added. During the period of addition, the reaction mixture was vigorously stirred. When the reaction reached about 90° C., 1,000 ml of toluene were added. Stirring continued for an additional one hour at 110° C. After the one hour, a gas chromatographic analysis was done and the conversion of mercaptan to disulfide did not exceed 10 percent. During the next 8 hours, the reaction continued without further conversion of the mercaptan to the disulfide.

Control

EXAMPLE 7

Preparation of bis(triethoxysilylpropyldisulfide)

In a 4-liter beaker, 691 grams (2.1 mole) of $K_3Fe(CN)_6$ and 1,000 ml of water were placed. Thereafter, 500 grams (2.1 mole) of 3-mercaptopropyl triethoxysilane were slowly added. During the period of addition, the reaction mixture was vigorously stirred. After 1 hour, a gas chromatographic analysis was done and the conversion of mercaptan to disulfide did not exceed 20 percent and a significant level of hydrolysis of the products was noted.

Control

EXAMPLE 8

Preparation of bis(triethoxysilylpropyldisulfide)

In a 2-liter beaker, 182 ml of 30 percent $H_2O_2$ solution (2.1 mole) were placed. Thereafter, 500 grams (2.1 mole) of 3-mercaptopropyl triethoxysilane were slowly added. During the period of addition, the reaction mixture was vigorously stirred. After 1 hour, a gas chromatographic analysis was done and the conversion of mercaptan to disulfide did not exceed 30 percent. The product was hydrolyzed and over-oxidized.

Control

EXAMPLE 9

Preparation of bis(triethoxysilylpropyldisulfide)

In a 4-liter beaker, 840 grams (4.2 mole) of $NaBO_3 \cdot 4H_2O$ in an aqueous methanol solution were placed. Thereafter, 500 grams (2.1 mole) of 3-mercaptopropyl triethoxysilane were slowly added. During the period of addition, the reaction mixture was vigorously stirred. After 1 hour, a gas chromatographic analysis was done and the conversion of mercaptan to disulfide did not exceed 20 percent and hydrolysis products were formed.

What is claimed is:

1. A process for the preparation of a organosilicon disulfide compounds of the formula $$Z-R^1-S_2-R^1-Z \qquad I$$

comprising oxidizing a compound of the formula $$Z-R^1-SH \qquad II$$

in the presence of a $MnO_2$, wherein Z is selected from the group consisting of $$-\underset{\underset{R^3}{|}}{\overset{\overset{R^2}{|}}{Si}}-R^2, \quad -\underset{\underset{R^3}{|}}{\overset{\overset{R^2}{|}}{Si}}-R^3 \quad \text{and} \quad -\underset{\underset{R^3}{|}}{\overset{\overset{R^3}{|}}{Si}}-R^3$$

wherein $R^2$ may be the same or different and is independently selected from the group consisting of an alkyl group having 1 to 4 carbon atoms and phenyl; $R^3$ may be the same or different and is independently selected from the group consisting of alkyl groups having 1 to 4 carbon atoms, phenyl, alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

2. The process of claim 1 wherein Z is $$-\underset{\underset{R^3}{|}}{\overset{\overset{R^3}{|}}{Si}}-R^3$$

$R^3$ selected from the group consisting of alkoxy groups having 1 to 2 carbon atoms and $R^1$ is an alkylene group having 1 to 3 carbon atoms.

3. The process of claim 1 wherein the molar ratio of the compound of formula II to $MnO_2$ ranges from 0.025 to 1:45.

4. The process of claim 2 wherein the molar ratio of the compound of formula II to $MnO_2$ ranges from 1:0.5 to 1:25.

5. The process of claim 1 wherein said disulfide of formula I is selected from the group consisting of 2,2'-bis(trimethoxysilylethyl) disulfide; 3,3'-bis(trimethoxysilylpropyl) disulfide; 3,3'-bis(triethoxysilylpropyl) disulfide; 2,2'-bis(tripropoxysilylethyl) disulfide; 2,2'-bis(triethoxysilylpropyl) disulfide; 3,3'-bis(triethoxysilylpropyl) disulfide; 2,2'-bis(trisec.butoxysilylethyl) disulfide; 3,3'-bis(tri-t-butoxyethyl) disulfide; 3,3'-bis(triisopropoxypropyl) disulfide; 3,3'-bis(trioctoxypropyl) disulfide; 2,2'-bis(2'-ethylhexoxysilylethyl) disulfide; 2,2'-bis(dimethoxy ethoxysilylethyl) disulfide; 3,3'-bis(methoxyethoxypropoxysilylpropyl) disulfide; 3,3'-bis(dimethoxymethylsilylpropyl) disulfide; 3,3'-bis(methoxy dimethylsilylpropyl) disulfide; 3,3'-bis(cyclohexoxy dimethylsilylpropyl) disulfide; 4,4'-bis(trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis(trimethoxysilylcyclohexyl) disulfide; 12,12'-bis(trimethoxysilyldodecyl) disulfide; 12,12'-bis(triethoxysilyldodecyl) disulfide; 18,18'-bis(trimethoxysilyloctadecyl) disulfide; 18,18'-bis(methoxydimethylsilyloctadecyl) disulfide; 2,2'-bis(trimethoxysilyl-2-methylethyl) disulfide; 2,2'-bis(triethoxysilyl-2-methylethyl) disulfide; 2,2'-bis(tripropoxysilyl-2-methylethyl) disulfide; 2,2'-bis(trioctoxysilyl-2-methylethyl) disulfide; 2,2'-bis(trimethoxysilyl-phenyl) disulfide; 2,2'-bis(triethoxysilyl-phenyl) disulfide; 1,1'-bis(trimethoxysilyl-tolyl)disulfide; 1,1'-bis(triethoxysilyl-tolyl)disulfide; 1,1'-bis(trimethoxysilyl-methyl tolyl) disulfide; 1,1'-bis(triethoxysilyl-methyl tolyl) disulfide; 2,2'-bis(trimethoxysilyl-ethyl phenyl) disulfide; 2,2'-bis(triethoxysilyl-ethyl phenyl) disulfide; 2,2'-bis(trimethoxysilyl-ethyl tolyl) disulfide; 2,2'-bis(triethoxysilyl-ethyl tolyl) disulfide; 3,3'-bis(trimethoxysilyl-propyl phenyl) disulfide; 3,3'-bis(triethoxysilyl-propyl phenyl) disulfide; 3,3'-bis(trimethoxysilyl-propyl tolyl) disulfide; and 3,3'-bis(triethoxysilyl-propyl tolyl) disulfide.

6. The process of claim 1 wherein said compound of formula II is selected from a group consisting of 2-mercaptoethyl trimethoxysilane, 3-mercaptopropyl trimethoxysilane; 2-mercaptopropyl triethoxysilane, 3-mercaptopropyl triethoxysilane, 2-mercaptoethyl tripropoxysilane, 2-mercaptoethyl tri sec.butoxysilane, 3-mercaptopropyl tri-t-butoxysilane, 3-mercaptopropyl triisopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyldimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyltriethoxysilane, 2-mercapto-2-methylethyltripropoxysilane, 2-mercapto-2-methylethyltrioctoxysilane, 2-mercaptophenyl trimethoxysilane, 2-mercaptophenyl triethoxysilane; 1-mercaptotolyl trimethoxysilane; 1-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

7. The process of claim 1 wherein said oxidation is in absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

8. The process of claim 1 wherein the oxidation reaction is conducted at a temperature ranging from 20° C. to 100° C.

9. The process of claim 8 wherein the oxidation reaction is conducted at a temperature ranging from 50° C. to 90° C.

10. The process of claim 1 wherein the oxidation reaction is conducted at a pressure ranging from 0.096 to 4.83 kg/cm$^2$.

* * * * *

UNITED STATES PATENT AND TRADEMARK OFFICE
CERTIFICATE OF CORRECTION

PATENT NO. : 5,440,064
DATED : August 8, 1995
INVENTOR(S) : Agostini et al

It is certified that error appears in the above-identified patent and that said Letters Patent is hereby corrected as shown below:

In claim 3, Column 12, line 64, delete 0.025 and insert therefor --1:0.025--.

Signed and Sealed this

Twenty-eighth Day of November 1995

Attest:

BRUCE LEHMAN

Attesting Officer

Commissioner of Patents and Trademarks